United States Patent [19]
Caldwell et al.

[11] 4,204,068
[45] May 20, 1980

[54] NITROGEN HETEROCYCLES

[75] Inventors: Albert G. Caldwell, West Wickham; Norman Whittaker, Beckenham, both of England

[73] Assignee: Burroughs Wellcome Co., Research Triangle Park, N.C.

[21] Appl. No.: 802,644

[22] Filed: Jun. 2, 1977

[30] Foreign Application Priority Data

| Jun. 3, 1976 [GB] | United Kingdom | 22877/76 |
| Dec. 2, 1976 [GB] | United Kingdom | 50340/76 |
| Jan. 1, 1977 [GB] | United Kingdom | 23071/77 |
| Mar. 23, 1977 [GB] | United Kingdom | 12145/77 |

[51] Int. Cl.² .................. C07D 233/76; C07D 233/78
[52] U.S. Cl. ..................... 548/313; 424/269; 424/273 R; 548/312; 548/253; 548/251
[58] Field of Search ............ 260/308 D; 548/312, 548/313

[56] References Cited

U.S. PATENT DOCUMENTS

| 2,786,850 | 3/1957 | Conroy | 548/313 |
| 4,147,796 | 4/1979 | Woolton | 424/273 R |

FOREIGN PATENT DOCUMENTS

| 38-25385 | 11/1963 | Japan | 548/313 |
| 45-31959 | 10/1970 | Japan | 548/313 |

*Primary Examiner*—Richard Raymond
*Attorney, Agent, or Firm*—Donald Brown

[57] ABSTRACT

Hydantoins and N-alkylhydantoins of formula (I)

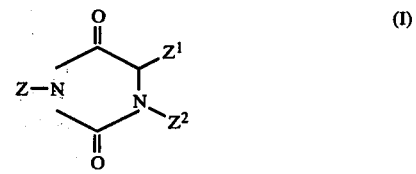

have biological properties related to those of naturally occurring prostaglandins and maybe used in medicine, for example in the treatment of thrombosis.

2 Claims, No Drawings

NITROGEN HETEROCYCLES

This invention relates to heterocyclic compounds, their synthesis, compositions containing them, and their use in medicine.

Hydantoin derivatives, defined hereinbelow in formula (I), have been found to have pharmacological properties related to those of natural prostaglandins, as demonstrated by their ability to mimic or antagonise the physiological effects of the natural prostaglandins in various biological preparations. In particular, certain compounds of formula (I) have been found to be potent mimmetics of the anti-platelet aggregatory properties of prostaglandin $E_1$.

In formula (I)

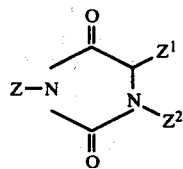

Z is hydrogen or alkyl; one of $Z^1$ and $Z^2$ is represented by the group $—CH_2—X—X^1—X^2$ wherein X is phenylene, $—C\equiv C—$, cis or trans $—CH=CH—$ or $—CH_2—CQ_2—$ in which each Q is independently selected from hydrogen and alkyl such as ethyl or the two Q's together form an alkylene radical having four, five or six carbon atoms; $X^1$ is a covalent bond or a straight or branched alkylene chain having 1 to 6 carbon atoms optionally having one of its methylene groups replaced by oxa(—O—) provided that at least one carbon atom seperates the oxa group from a $—C\equiv C—$, $—CH=CH—$ or $—CO—$ group; and $X^2$ is selected from 5-tetrazolyl, carboxyl, carboxamide, hydroxymethylene and alkoxycarbonyl;

and the other of $Z^1$ and $Z^2$ is represented by the group $—Y—Y^1—Y^2—Y^3$ wherein Y is $—CR_2—CH_2—$ in which each R is independently selected from hydrogen and methyl; $Y^1$ is carbonyl, methylene, methylene substituted by hydroxyl or methylene substituted by hydroxyl and alkyl; $Y^2$ is a covalent bond or straight or branched alkylene having 1 to 7 carbon atoms optionally substituted on the carbon adjacent $Y^1$ by one or two groups independently selected from alkyl, bicycloalkyl cycloalkyl; $Y^3$ is hydrogen, hydroxy, alkoxy having 1 to 7, preferably 1 to 4, carbon atoms; cycloalkyl, bicycloalkyl, phenyl, benzyl, phenoxy or benzyloxy, wherein each of phenyl, benzyl, phenoxy and benzyloxy may be substituted in the benzene ring by one or more groups selected from hydroxy, halogeno, nitro, amino, acylamino, alkenyl, alkoxy, phenyl and alkyl which may itself be substituted by one or more halogeno groups; or Y is a bond, $—CH_2—$, or $—CH_2.CH_2—$ and $Y^1$, $Y^2$ and $Y^3$ taken together form a cycloalkyl group substituted by a hydroxyl group which preferably has three carbon atoms separating it from the hydantoin ring.

Unless otherwise stated, in formula (I) and other formulae in this specification, alkyl moieties are selected from methyl, ethyl, propyl, butyl, pentyl and hexyl, including all isomers thereof;

For example, in the definitions of $Y^1$ and $Y^2$ the alkyl groups are preferably methyl; and the alkyl moiety of alkoxycarbonyl is desirably methyl or ethyl. Similarly alkylene groups have 2 to 4 carbon atoms for example vinyl.

In formula (I) cycloalkyl groups have 3 to 10 carbon atoms and bicycloalkyl groups have 4 to 10 carbon atoms for example adamantyl.

In a compound of formula (I) the bonding of the divalent phenylene group may be ortho, meta or para, and the oxa group is preferably adjacent the phenylene or when X is other than phenylene then $X^1$ may be $—CH_2—O—CH_2—$.

Included in the meaning of compounds of formula (I) are the salts corresponding to the carboxylic acids and tetrazoles when $X^2$ is carboxyl or tetrazolyl respectively, and the salts which may also be formed when Z is hydrogen. Particularly valuable salts for medical purposes are those having a pharmaceutically acceptable cation such as ammonium or that of an alkali metal eg. sodium and potassium, an alkaline earth metal eg. calcium and magnesium, or an organic base, particularly an amine such as ethanolamine. Salts having non-pharmaceutically cations are included within the ambit of this invention as useful intermediates to pharmaceutically acceptable salts, or the acids or esters of formula (I).

Except when there is clear indication to the contrary, formula (I) and other formulae in the specification embrace all stereoisomers represented therein. In particular such formulae include the enantiomeric forms, such mixtures as are designated racemates, and diastereoisomers.

It has been found that compounds of formula (I) wherein

Z is hydrogen or alkyl having 1 to 4 carbon atoms, for example methyl or butyl;

one of $Z^1$ and $Z^2$ is $—CH_2—X—X^1—X^2—$ wherein X and $X^1$ taken together form alkylene of 3 to 7 in particular 5 carbon atoms, and $X^2$ is alkoxycarbonyl, carboxyl or a salt thereof;

and the other of $Z^1$ and $Z^2$ is $—Y—Y^1—Y^2—Y^3—$ wherein Y, $Y^1$ and $Y^2$ are as hereinbefore defined and $Y^3$ is hydrogen, phenyl or benzyl, or $Y^2$ and $Y^3$ together form cycloalkyl of 4 to 7 carbon atoms; have particularly interesting prostaglandin-related properties. Within this definition are included the subclass wherein Z is hydrogen and $Z^1$ is $—CH_2—X—X^1—X^2—$ as defined.

The compounds of formula (I) may be synthesised by any method known in the art for the synthesis of compounds of analogous structure. For example, they may be prepared from the corresponding derivatives of hydantoic acid of formula (II)

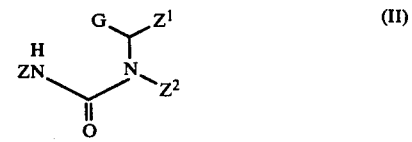

wherein G is carboxyl or a derivative thereof such as amide or ester in particular an alkyl ester, and each of Z, $Z^1$ and $Z^2$ has the same meaning as in formula (I), by cyclisation under acidic conditions or by heating alone. The reaction may be effected in the absence of a solvent, but if desired an inert solvent may be used, for example a hydrocarbon such as petrol. Alternatively, where G is alkoxycarbonyl, cyclisation may be effected in the presence of a suitable base, for example an alkoxide such as sodium ethoxide.

Compounds of formula (II) are conveniently prepared from an amino acid derivative of formula (III)

(III)

wherein G, $Z^1$ and $Z^2$ are as defined in formula (I) provided that G may also be nitrile by reaction with cyanic acid or an alkyl iso-cyanate depending respectively on whether Z is hydrogen or alkyl.

When cyanic acid is used, the cyanic acid is conveniently produced in situ by the use of an alkali metal cyanate, eg. potassium cyanate, and an acid which may be present as an acid addition salt of the compound of formula (III) or a free acid of formula (III) wherein either or both of R and $X^2$ is hydrogen. Alternatively an equivalent amount of mineral acid or an organic acid may be added to the reaction medium. The reaction may proceed in the absence of a solvent but desirably an inert solvent is used which is preferably polar such as water or a mixture of water with acetone dimethylformamide, dimethylsulphoxide or a lower alkanol such as ethanol or it may be a hydrocarbon, an ether or halogenated hydrocarbon such as chloroform. Where desired, for example if no solvent is used, the reaction may be promoted by heating the reactants.

Similar reaction conditions may be used when an alkyl isocyanate is used except that it is unnecessary to provide an equivalent amount of acid, as an acid addition salt or otherwise, in the reactants.

Instead of using a cyanate or isocyanate, a compound of formula (III) may be reacted with urea, nitrourea or an N-alkylurea as appropriate. A solvent is not essential but if desired an inert solvent such as one mentioned above may be used, and the reaction is preferably effected at an elevated temperature, for example from 100° to 125° C. but temperatures upto 150° C. may be employed.

In the above described synthesis, the intermediates of formula (II) need not be isolated from the reaction mixture and may be converted directly to compounds of formula (I) under the described reaction conditions.

An intermediate of formula (III) may be conveniently prepared by reaction of a compound of formula (IV) with a compound of formula (V)

(IV)

$Q^2-Z^2$ (V)

wherein G, $Z^1$ and $Z^2$ are as defined in formula (III), one of $Q^1$ and $Q^2$ is amino and the other is halogeno, preferably bromo. The reaction may be carried out by heating in the absence of solvent or in the presence of an inert solvent such as ethanol.

The intermediates of formula (III) wherein $Z^2$ is $-Y-Y^1-Y^2-Y^3$ when $Y^1$ is carbonyl may also be prepared by reaction of an amine of formula (IV) wherein $Q^1$ is amino with an unsaturated ketone of formula (VI)

$CR_2=CH.CO.Y^2.Y^3$ (VI)

wherein $Y^2$ and $Y^3$ have the same meaning as in formula (III); the reaction being effected in the presence or absence of an inert solvent, and at room temperature or optionally with heating.

Hydantoins of formula (I) may also be prepared by cyclisation of a compound of formula (VII)

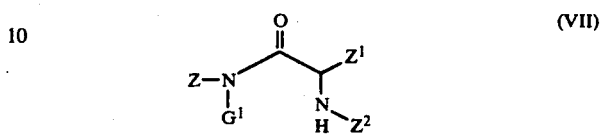
(VII)

wherein Z, $Z^1$ and $Z^2$ are as defined in formula (I) and $G^1$ is carboxyl or a reactive derivative thereof such as alkoxycarbonyl eg. ethoxycarbonyl. Compounds of formula (VII) may be cyclised under similar conditions as a compound of formula (II) and conveniently the method used to prepare a compound of formula (VII) is chosen such that the prevailing reaction conditions permit spontaneous cyclisation.

For example, the intermediates of formula (VII) may be prepared by reacting a compound of formula (V) with a compound of formula (VIII)

$Q^2-Z^2$ (V)

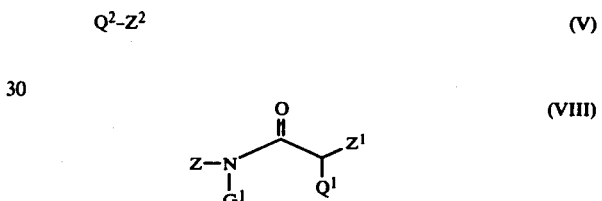
(VIII)

wherein one of $Q^1$ and $Q^2$ is halogeno, preferably chloro or bromo and the other is amino and each of Z, $Z^1$, $Z^2$ and $G^1$ have the same meaning as in formula (VII). The reaction may be effected by admixture of the reactants or optionally an inert solvent is used and the mixture is heated. Suitable solvents include alkanols, ethers, hydrocarbons and halogenated hydrocarbons.

The compounds of formula (VIII) may themselves be made by reacting an appropriate carbamic acid derivative, for example an alkyl ester, with a compound of formula (IV), using techniques known to those skilled in the art.

In a method related to those described hereinbefore, the hydantoins of formula (I) may be prepared by reacting a compound of formula (IX)

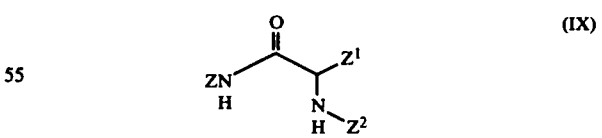
(IX)

wherein each of Z, $Z^1$ and $Z^2$ has the same meaning as in formula (I) with a carbonic acid derivative. Any carbonic acid derivative known to those skilled in the art as appropriate may be used, for example phosgene, diphenylcarbonate or an alkyl haloformate such as ethyl chloroformate. The reaction is desirably effected in the presence of a base, for example an amine such as triethylamine or di-iso-propyl ethylamine, and using an inert aprotic solvent such as toluene, dimethylformamide or an ether such as diethylether. The reaction may be carried out at room temperature but if desired the reaction mixture may be heated.

The intermediates of formula (IX) may be made using methods analogous to those described above for the preparation of compounds of formula (III).

The hydantoins of formula (I) wherein Z is alkyl may also be prepared by alkylation, using an alkylating agent which may be designated as a reactive ester derivative of an alcohol $J^3 \cdot OH$, of a compound of formula (X)

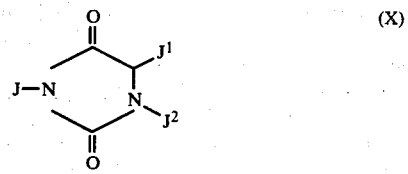

wherein J is hydrogen or alkyl, $J^1$ is hydrogen or $Z^1$, $J^2$ is hydrogen or $Z^2$ and $J^3$ is alkyl, $Z^1$ or $Z^2$, provided that one of J, $J^1$ and $J^2$ is hydrogen and $J^3$ does not have the same value as J, $J^1$ or $J^2$; in the definition of $J^1$, $J^2$ and $J^3$ each of $Z^1$ and $Z^2$ has the same meaning as in formula (I). Suitable reactive ester derivatives include chloride, bromide, iodide and sulphonates such as p-toluenesulphonate, methanesulphonate and benzenesulphonate. The alkylation may be effected using reaction conditions which are known in the art to be suitable, for example in the presence of a base such as an alkalimetal hydride, alkali metal amide, or alkalimetal alkoxide, typically sodium hydride or a sodium alkoxide e.g. sodium methoxide.

The reaction is conveniently carried out in an inert solvent which simply acts as a diluent for the reactants such as toluene, dioxan, ether, dimethyl formamide, tetrahydrofuran, dimethylsulphoxide or acetonitrile or when the base is an alkali metal alkoxide then the corresponding alkanol may be used.

It will be appreciated that the intermediates of formula (X) wherein J is hydrogen are also compounds of formula (I) and may be prepared by one of the foregoing methods. The compounds of formula (X) may further be prepared by adaptation of methods already known in the art (see for example Chemical Reviews (1950) 46, p. 403-425).

A further preparation of compounds of formula (I) is by reduction of a corresponding unsaturated compound of formula (XI)

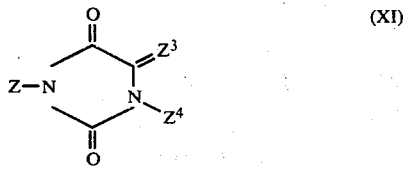

wherein either $Z^3$ is $=CR-CH_2-Y^1-Y^2-Y^3$ and $Z^4$ is $-CH_2-X-X^1-X^2$ or $Z^3$ is $=CH-X-X^1-X^2$ and $Z^4$ is $-Y-Y^1-Y^2-Y^3$ in which each of R, X to $X^2$ and Y to $Y^3$ is as defined in formula (I), with a suitable reducing agent.

A suitable reducing agent is stannous chloride which may be used as an aqueous solution optionally in the presence of dilute mineral acid or catalytic hydrogenation may be effected in the presence of for example Raney nickel, platinum, palladium, ruthenium or rhodium. The choice of reducing agent in a given situation will of course be dictated by the presence of other reactive groups in the molecule which may themselves be susceptible to reduction.

The intermediates of formula (XI) may be prepared by the following series of reaction:

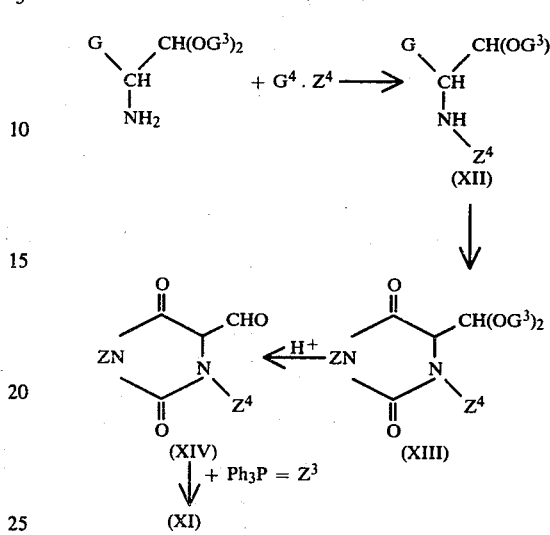

(XI)

In the above formulae Z, $Z^3$, $Z^4$ and G have the same meanings as in formulae (XI) and (III) respectively, $G^3$ is alkyl for example n-butyl and $G^4$ is halogeno such as bromo. The formation of (XIII) is analogous to the ring closure involving a compound of formula (II) and compounds of formula (XIV), are prepared using concentrated mineral acid such as hydrochloric acid.

Tetrazoles of formula (I) may be prepared from corresponding compounds wherein the group $-X^2$ is replaced by $$-\underset{X^4}{C}=\underset{X^3}{N}$$

wherein $X^3$ and $X^4$ together form a bond (nitrile), $X^3$ is hydrogen or alkyl and $X^4$ is alkoxy (imidoester), alkylthio (imidothioester), $-NH-NH_2$ (amidrazone), or amino (amidine) or $R^3$ is hydroxy and $R^4$ is amino (amidoxime). The reaction is preferably carried out in a polar aprotic liquid medium such as dimethylformamide using a salt of a hydrazoic acid e.g. sodium azide. However, when $X^2$ is replaced by an amidine or amidrazone, a suitable reagent is nitrous acid. If an amidine is reacted with nitrous acid then reduction of the intermediate nitrosation product, with or without prior isolation, using for example sodium amalgam is required to give the corresponding tetrazole. The tetrazole precursor may be obtained by well known methods, for example the nitrile may be obtained by dehydration of the corresponding amide.

The alcohols of formula (I) wherin $X^2$ is hydroxymethylene may also be obtained by reduction with an appropriate reducing agent of the corresponding acid, ester, acid halide, acid anhydride or aldehyde. The appropriate reducing agent will depend on the particular substrate, but reactants which may be used are sodium in ethanol. In particular a carboxylic acid may for example be converted to a corresponding mixed anhydride with ethylchloroformate in the presence of a base as triethylamine, and subsequently reduced to the alcohol using sodium borohydride. Similarly an ester may be reduced to the alcohol using di-iso-butyl aluminum hydride in an inert solvent such as ether or hydrocarbon such as hexane or benzene. Such alcohols may also be prepared by catalytic hydrogenation.

Alternatively the alcohols of formula (I) wherein $X^2$ is hydroxymethylene may be prepared by hydrolysis of a corresponding halide with an appropriate reagent. For this purpose a hydroxide may be used for example an aqueous alkali or a suspension of silver oxide in water.

In the synthesis of hydantoins of formula (I) having a hydroxyl group in a side chain it may be desirable to protect this during the course of the reaction. This may be readily effected in known manner using a protecting group such as acyl, aroyl, tetrahydropyran-2-yl, 1-ethoxyethyl or aralkyl, for example benzyl.

Removal of protecting groups may be carried out by appropriate methods known to those skilled in the art: for example an acyl group may be removed by acid or base hydrolysis, and a benzyl group by reductive cleavage.

Furthermore a ketone of formula (I) wherein $Y^1$ is carbonyl may be converted to the corresponding secondary alcohol by reduction with a suitable reducing agent, such as sodium borohydride. Also, an alcohol of formula (I) wherein $Y^1$ is —CH.OH— may be oxidised to the corresponding ketone using Jones' reagent, acid dichromate or any other suitable reagent.

Similarly where the compounds of formula (I) have a C≡C or CH=CH bond these may be converted by conventional hydrogenation techniques, for example using a Lindlar type or Adams catalyst, to the corresponding ethylenic or saturated compounds as appropriate.

The hydantoins of formula (I) have an asymmetric 5-carbon atom, and a further asymmetric centre is present in those compounds wherein $Y^1$ includes a hydroxyl group. Such alcohols therefore exist as four isomers which are separable by thin layer chromatography or high performance liquid chromatography into two diastereomers, each of which is a racemic mixture of two isomers. On separation of the diastereomers one diastereomer may be converted to a mixture of the four isomers by treatment with a base, such as an alkali metal hydroxide, and subsequently re-separated to provide two diastereomers. Repeated use of this technique enables the effectual conversion of one diastereomer to the other; this may be desirable when one diastereomer has a biological activity preferred to the other.

The corresponding alcohols of formula (III) also exist in four isomeric forms. If desired, these may be separated into two epimers and subsequent cyclisation to a compound of formula (I) retains the stereochemical configuration.

In all of the foregoing chemical procedures it is of course evident that the choice of reactant will be dictated in part by the functional groups present in the substrate, and where necessary reactants having an appropriate selectivity of action must be used.

The hydantoins of formula (I) are of value in having pharmacological properties related to those of natural prostaglandins; that is, the hydantoins mimic or antagonise the biological effects of members of the prostaglandin (PG) 'A', 'B', 'C', 'D', 'E' and 'F' series. For example, hydantoins of formula (I) have been found to mimic the antiaggregatory effect of $PGE_1$ on blood platelets, and to antagonise the contraction induced by $PGE_2$ or $PGF_2$ on smooth muscle taken from the rat stomach, rat colon, chick rectum and guinea pig trachea. In general, antagonistic properties, as opposed to mimetic, have been observed when using larger doses of the hydantoins. The pharmacological profile, by which is meant the relative activities, mimetic or antagonistic, compared with the natural prostaglandins, will of course vary depending on the specific hydantoin under consideration.

By reason of their prostaglandin-related properties, the hydantoins of formula (I) are useful in the pharmacological characterisation and differentiation of the biological activities of the natural prostaglandins and their 'receptors'. The further understanding of the physiological role of prostaglandins is of course valuable in the search for new and improved therapeutic substances.

The hydantoins of formula (I) are also of value as therapeutic agents. In particular hydantoins such as those described previously as having a potent anti-aggregatory effect on blood platelets are useful whenever it is desired to inhibit platelet aggregation or to reduce the adhesive character of platelets, and may be used to treat or prevent the formation of thrombi in mammals, including man. For example, the compounds are useful in the treatment and prevention of myocardial infarcts, to treat and prevent thrombosis, to promote patency of vascular grafts following surgery, and to treat complications of arteriosclerosis and conditions such as atherosclerosis, blood clotting defects due to lipermia, and other clinical conditions in which the underlying aetiology is associated with lipid imbalance or hyperlipidemia. A further use for such compounds is as an additive to blood and other fluids which are used in artificial extra-corporeal circulation and perfusion of isolated body portions.

A group of compounds which have been found particularly valuable as inhibitors of platelet aggregation are those of formula (I) wherein Z is hydrogen; $Z^1$ is carboxyalkylene wherein the alkylene moiety has 3 to 9 carbon atoms; and $Z^2$ is a group —$(CH_2)_2.CH.OH.Y^2.Y^3$ wherein $Y^2$ is branched alkylene having a tertiary carbon atom adjacent the hydroxy-substituted carbon and $Y^3$ is as defined in formula (I), or $Y^2$ and $Y^3$ together form cycloalkyl having 3 to 10 carbon atoms. Within this group of compounds, those wherein $Z^1$ is carboxyhexyl and $Y^2$ and $Y^3$ together form cycloalkyl having 4 to 7 carbon atoms have been found especially active.

It has also been found that hydantoins of formula (I) cause relaxation of vascular smooth muscle in a similar way as do members of the prostaglandin 'A' and 'E' series. Examples of such compounds are 5-(6-carboxyhexyl)-1-(3-hydroxy-4,4-dimethyloctyl)hydantoin and 5-(6-carboxyhexyl)-1-(3-hydroxy-4,4-dimethyl-5-phenylpentyl)hydantoin. Compounds relaxing vascular smooth muscle are capable of inducing vasodilation and therefore have antihypertensive properties and are useful in lowering blood pressure in mammals, including man, and may be used alone or in combination with a β-adrenoceptor blocking agent or another antihypertensive substance for the treatment of all grades of hypertension including essential, malignant and secondary hypertension.

The compound 5-(6-carboxyhexyl)-1-(3-hydroxy-4,4-dimethyloctyl)hydantoin also mimics the effect of PGE, of antagonising histamine induced broncho-constriction. The hydantoins of formula (I) having this property may be used in the treatment or prophylaxis of bronchial asthma and bronchitis by alleviating the bronchoconstriction associated with this condition.

Hydantoins of formula (I), such as 5-(6-carboxyhexyl)-1-(3-hydroxyoctyl)-hydantoin, 5-(6-carboxyhexyl)-3-methyl-1-(3-oxo-octyl)hydantoin, 5-(6-carboxyhexyl)-1-(3-oxo-octyl)hydantoin and 5-(6-carboxyhexyl)-1-(4-phenoxybutyl)hydantoin, which inhibit pentagastrin-induced gastric acid secretion and reduce the formation of aspirin-induced gastric lesions in rats are useful in reducing excessive gastric secretion, reducing and avoiding gastro-intestinal ulcer formation and accelerating the healing of such ulcers already present in the gastrointestinal tract whether such ulcers arise spontaneously or as a component of polyglandular adenoma syndromes.

Intravenous infusions of certain hydantoins of formula (I), typically 5-(6-carboxyhexyl)-1-(3-hydroxyoctyl)hydantoin, to dogs has been found to increase urine volume indicating a potential utility for such compounds as diuretic agents, the uses of which include the treatment of oedema for example oedema associated with heart failure, liver failure or kidney failure in man or other mammals.

A further use for hydantoins of formula (I) which mimic the uterine smooth muscle effects of $PGE_2$ and $PGF_{2\alpha}$ is as antifertility agents, in particular as abortifacients.

The amount of a compound of formula (I) required to achieve the desired biological effect will of course depend on a number of factors, for example, the specific compound chosen, the use for which it is intended, the mode of administration, and the recipient. In general, a daily dose may be expected to lie in the range of from 1 $\mu$g to 20 mg per kilogram bodyweight. For example, an intravenous dose may lie in the range of from 5 $\mu$g to 1 mg/kg which may conveniently be administered as an infusion of from 0.01 to 50 $\mu$g per kilogram per minute. Infusion fluids suitable for this purpose may contain from 0.001 to 100, for example from 0.01 to 10 $\mu$g per millilitre. Unit doses may contain from 10 $\mu$g to 100 mg of a compound of formula (I), for example ampoules for injection may contain from 0.01 to 1 mg, and orally administrable unit dose formulations such as tablets or capsules may contain from 0.1 to 50, for example 2 to 20 mg.

More specifically, when a compound of formula (I) is used to inhibit platelet aggregation it is generally desirable to achieve a concentration in the appropriate liquid, whether it be the blood of a patient or a perfusion fluid, of about 1 $\mu$g to 10 mg, for example from 10 $\mu$g to 1 mg, per liter.

The abovementioned doses refer to the acids, amides, esters, alcohols and tetrazoles of formula (I); where a salt is used, the dose should be taken as referring to the corresponding anion.

For use in the treatment or prophylaxis of the conditions referred to above, while the hydantoin compounds may be used as the raw chemical they are preferably presented with an acceptable carrier therefor as a pharmaceutical formulation. The carrier must of course be 'acceptable' in the sense of being compatible with the other ingredients of the formulation and not deleterious to the recipient thereof. The carrier may be a solid or a liquid, and is preferably formulated with a hydantoin compound as a unit-dose formulation, for example a tablet, which may contain from 0.05% to 95% by weight of the hydantoin compound. Other pharmacologically active substances may also be present in formulations of the present invention as indicated above. The hydantoin compounds may be incorporated in the formulations either in the form of the acid or the salt or ester thereof, and the formulations may be prepared by any of the well-known techniques of pharmacy consisting essentially of admixture of the components of the formulation.

The formulations include those suitable for oral, rectal, topical (buccal - eg. sub-lingual), the parenteral (that is subcutaneous, intramuscular and intravenous) administration, although the most suitable route in any given case will depend on the nature and severity of the condition being treated, and on the nature of the hydantoin compound.

Formulations suitable for oral administration may be presented as discrete units such as capsules, cachets, lozenges or tablets each containing a predetermined amount of hydantoin compound; as a powder or granules; as a solution or a suspension in an aqueous liquid or a non-aqueous liquid; as an oil-in-water emulsion; or as a water-in-oil liquid emulsion. Such formulations may be prepared by any of the methods of pharmacy but all methods include the step of bringing into association the hydantoin compound with the carrier which constitutes one or more accessory ingredients. In general they are prepared by uniformly and intimately admixing the hydantoin compound with liquid or finely divided solid carriers or both, and then, if necessary, shaping the product into the desired presentation. For example a tablet may be prepared by compression or moulding a powder or granules of the hydantoin compound, optionally with one or more accessory ingredients. Compressed tablets may be prepared by compressing, in a suitable machine, the hydantoin compound in a free-flowing form such as a powder or granules optionally mixed with a binder, lubricant, inert diluent, surface active or dispersing agent(s). Moulded tablets may be made by moulding in a suitable machine the powdered hydantoin compound moistened with an inert liquid diluent.

Formulations suitable for buccal (sub-lingual) administration include lozenges comprising a hydantoin compound in a flavoured basis, usually sucrose and acacia or tragacanth; and pastilles comprising a hydantoin compound in an inert basis such as gelatin and glycerin; or sucrose and acacia.

Formulations of the present invention suitable for parenteral administration conveniently comprise sterile aqueous preparations of a hydantoin compound, which preparations are preferably isotonic with the blood of the intended recipient. These preparations are preferably administered intravenously, although administration may also be effected by means of subcutaneous or intramuscular injection. Such preparations may be conveniently prepared by admixing the hydantoin compound with water and rendering the product sterile and isotonic with the blood.

Formulations suitable for rectal administration are preferably presented as unit-dose suppositories. These may be prepared by admixture of the hydantoin compound with one or more of the conventional solid carriers, for example cocoa butter, and shaping of the resulting mixture.

It will be appreciated from the foregoing that what we will claim may comprise any novel feature described herein, principally and not exclusively, for example:
(a) The novel compounds of formula (I) as hereinabove defined.

(b) A method for the preparation of the novel compounds of formula (I) as hereinabove described.

(c) A pharmaceutical formulation comprising a compound of formula (I) in association with a pharmaceutically acceptable carrier therefor, and methods for the preparation of such formulations.

(d) A method for lowering blood pressure in a mammal including man which comprises administration to the mammal of an effective hypotensive, non-toxic amount of a compound of formula (I).

(e) A method for the treatment or prophylaxis of thrombosis in a mammal or mammalian tissue, including human, which comprises administration of a non-toxic, effective anti-thrombotic amount of a compound of formula (I).

(f) A method for inducing vasodilation in a mammal, including man, comprising administration to said mammal of a non-toxic effective vasodilatory amount of a compound of formula (I).

(g) A method for the treatment or prophylaxis of gastric lesions in a mammal including man comprising administration to said mammal of a non-toxic effective prophylactic or therapeutic amount of a compound of formula (I).

(h) A method for inducing bronchodilation in a mammal, including man, comprising administration to said mammal of a non-toxic, effective bronchodilatory amount of a compound of formula (I).

(i) A method for the treatment or prophylaxis of an allergic condition in a mammal, including man, comprising administration to said mammal of a non-toxic effective prophylactic or therapeutic amount of a compound of formula (I).

(j) A method of inducing abortion of a foetus in a mammal including human comprising administration to said mammal of a non-toxic effective abortifacient amount of a compound of formula (I).

(k) A method of inducing infertility in a mammal including human comprising administration to said mammal of a non-toxic effective contraceptive amount of a compound of formula (I).

(l) A compound of formula

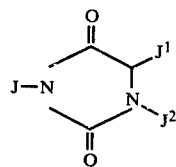

wherein two of J, $J^1$ and $J^2$ are the same as two of Z, $Z^1$ and $Z^2$ as hereinbefore defined in formula (I) respectively, and the other is hydrogen.

(m) A compound of formula

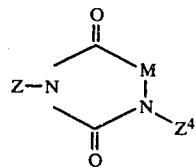

wherein M represents $>C=Z^3$, $>CH-CHO$ or $>CH-CH(OG^3)_2$ and Z, $Z^3$, $Z^4$ and $G^3$ are as hereinbefore defined in formulae (XI) and (XII) respectively.

(n) A compound of formula

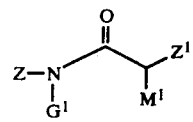

wherein $M^1$ represents $-Q^1$, as defined in formula (VIII), or $-NH-Z^2$ and Z, $Z^1$, $Z^2$ and $G^1$ are as defined in formula (VII) except that $G^1$ may also be hydrogen.

EXAMPLE 1

Preparation of
5-(6-Carboxylhexyl)-1-(3-hydroxy-4,4-dimethyl-5-phenylpentyl)hydantoin A. Diethyl 2-aminononanediote Diethyl acetamidomalonate (16.7 g) and ethyl 7-bromoheptanoate (16.6 g) were dissolved in ethanolic ethoxide (prepared from sodium (1.51 g) and absolute ethanol (30 ml)) and the mixture was refluxed for 27 hours. The cooled solution was poured into ice-water, the product was extracted into ether, and the dried extract was evaporated to give crude diethyl acetamido-(6-ethoxycarbonylhexyl) malonate as a pale yellow oil, δ2.2(3H, singlet, —COCH₃), 4.17(6H, multiplet, 3×—OCH₂—CH₃). This amide was refluxed with concentrated hydrochloric acid (111 ml) for 5¼ hours, the cooled solution was washed with ether, and the aqueous layer was decolorised with activated charcoal and evaporated to dryness in vacuo. The residual colourless glass was dissolved in the minimum quantity of absolute ethanol and added dropwise to a stirred, cooled (−10° C.) mixture of absolute ethanol (125 ml) and thionyl chloride (15.7 g). The resulting solution was set aside at room temperature for 1 hour, refluxed for 1¼ hours, cooled, and poured into ice-water adjusting the pH to 9 with aqueous sodium hydroxide. The mixture was extracted with ether, and the dried extract was concentrated and distilled, giving diethyl 2-aminononanedioate (55% yield) as a colourless oil, b.p. 114°–115°/0.02—0.3 mm.

B. Diethyl
2-((4,4-dimethyl-3-oxo-phenylpentyl)amino)nonanediote

To diethyl 2-aminononanedioate (5.18 g) was added dropwise 4,4-dimethyl-5-phenylpent-1-en-3-one (3.95 g) with cooling and stirring. The mixture was allowed to stand at room temperature for 21 hours to give diethyl 2-(4,4-dimethyl-3-oxo-5-phenylpentyl)amino)nonanedioate.

C. Diethyl
2-(3-hydroxy-4,4-dimethyl-5-phenylpentyl)amino)nonanedioate

The foregoing crude ketone (5.1 g) was dissolved in absolute ethanol (70 ml) and the solution was stirred in an ice-bath during the gradual addition of sodium borohydride (380 mg). The solution was stirred in the ice-bath for a further 10 minutes and then left to stand at room temperature for 5 hours. Most of the alcohol was evaporated, water was added, and the solution acidified to pH 6. The insoluble oil was extracted with ether, and the ether solution was dried and evaporated to leave diethyl 2-(3-hydroxy-4,4-dimethyl-5-phenylpentyl- )amino)nonanedioate as a pale yellow oil which was used without further purification.

D.
5-(6-Ethoxycarbonyl-hexyl)-1-(3-hydroxy-4,4-dimethyl-5-phenylpentyl)hydantoin and the corresponding acid A solution of the above alcohol (8.45 g) in ethanol (37.6 ml) and 2 N-hydrochloric acid (18.8 ml) was stirred and cooled in ice during the dropwise addition of a solution of potassium cyanate (3.05 g) in water (5.6 ml). The mixture was allowed to stand at room temperature for 18 hours, then the alcohol was evaporated, water was added and the insoluble oil was extracted with ether. The dried ether solution was evaporated to leave a viscous oil which was heated on the steam bath for 6 hours to give 5-(6-ethoxycarbonylhexyl)-1-(3-hydroxy-4,4-dimethyl-5-phenylpentyl)hydantoin as a viscous pale yellow oil.

This ester was added to a mixture of 2 N-sodium hydroxide (25 ml) and water (60 ml) and the resulting cloudy solution was left at room temperature for 2 hours. The solution was washed with ether and the clear alkaline solution was acidified with 2 N-hydrochloric acid and the precipitated oil was extracted with ether. Evaporation of the dried ether solution gave a viscous oil (6.8 g) which was chromatographed on a column of silica gel to give 5-(6-carboxyhexyl)-1-(3-hydroxy-4,4-dimethyl-5-phenylpentyl)-hydantoin as a colourless viscous oil which solidified, m.p. ca. 115° C., shrinking from ca. 90° C. being a mixture of diastereomers. Recrystallisation several times from a mixture of ethyl acetate and light petroleum (b.p. 60°-80° C.) gave one of the diastereomers as small needles, m.p. 135°-137° C.

EXAMPLE 2
Preparation of 5-(6-Carboxyhexyl)-1-(3-hydroxyoctyl)hydantoin

A. Diethyl 2-(3-(tetrahydropyran-2-yloxy)octylamino)nonanedioate

Dry ethereal hydrogen bromide, prepared from ether (200 ml) and hydrogen bromide (26.8 g) at 0° C., was added dropwise to a stirred solution of acrolein (19.15 g) in ether (100 ml) cooled to −25° C. The stirred mixture was kept at this temperature for 1 hour, allowed to come to 0° C., stirred for 1 hour, at 0° C. and then added dropwise to ethereal pentyl magnesium bromide (prepared from 1-bromopentane (54 g) magnesium (8.8 g) and ether (120 ml)), maintaining constant reflux. The reaction mixture was decomposed with saturated aqueous ammonium chloride and extracted with ether, and the dried extract was concentrated and distilled, giving 1-bromo-3-hydroxyoctane as a colourless oil, b.p. 68.5°-72.5° C./0.08 mm. A solution of this bromo-alcohol (20.9 g) in dihydropyran (17.0 g), was treated with p-toluenesulphonic acid (500 mg) in a little ether, set aside at room temperature for 18 hours, and washed with aqueous sodium bicarbonate. The organic layer was percolated through silica in 1:9 ether/hexane and the solvent was removed in vacuo, giving 1-bromo-3-(tetrahydropyran-2-yloxy)octane as a colourless oil, δ0.88(3H, triplet, —CH$_3$) and 4.62(1H, broad, -O-CHR-O-). A solution of this tetrahydropyranyl intermediate (15.0 g) and diethyl 2-aminononanedioate (13.0 g) in absolute ethanol (100 ml) was refluxed for 18 hours, the ethanol was removed in vacuo, and the residue was diluted with water containing a slight excess of sodium carbonate. The mixture was extracted with dichloromethane, the extract was dried over sodium sulphate and evaporated, and the residue was purified by column chromatography on silica in 1:4 hexane/ether, giving diethyl 2-(3-(tetrahydropyran-2-yloxy)octylamino)nonanedioate as a colourless viscous oil, δ0.88(3H, triplet —CH$_3$), 2.28(2H, triplet, -CH$_2$-CO$_2$Et), 2.61(2H, multiplet, -CH$_2$-N), 3.20(1H, triplet, N—CHR—CO$_2$Et), 4.13(4H, multiplet, 2×-O-CH$_2$-CH$_3$), 4.60(1H, broad -O-CHR-O-).

The above aminodiester was alternatively prepared in the following manner. Diethyl 2-aminononanedioate (10.40 g) and oct-1-en-3-one (5.04 g) were mixed slowly at 0° C. with stirring, and set aside at room temperature for 3 hours, giving diethyl 2-(3-oxooctylamino)nonanedioate as a colourless oil, δ2.3(4H, multiplet, -CH$_2$-CO$_2$Et and NCH$_2$CH$_2$CO-), 3.16(1H, triplet, EtO$_2$C-CHR-N), 4.11(2H, quartet, —O—CH$_2$—CH$_3$), 4.17(2H, quartet, -O-CH$_2$-CH$_3$). A stirred solution of this ketone (13.5 g) in absolute ethanol (140 ml) was treated dropwise at 0° C. with sodium borohydride (665 mg) in absolute ethanol (70 ml), then kept for 3½ hours at room temperature and concentrated at 40° C. in vacuo. The residue, dissolved in water, was brought to pH 5 with N-hydrochloric acid and extracted thoroughly with chloroform, the extract was washed with water, dried, and evaporated, giving diethyl 2-(3-hydroxyoctylamino)nonanedioate as a colourless oil. Without further purification, the latter was dissolved in dihydropyran (14.0 ml), treated with ether (10 ml) followed by p-toluenesulphonic acid (6.72 g) in portions, and set aside at room temperature for 18 hours. The reaction solution was diluted with ether, washed with aqueous sodium carbonate then water, dried, and evaporated, and the residue was purified by column chromatography on silica in 1:4 hexane/ether, giving diethyl 2-(3-(tetrahydropyran-2-yloxy)octylamino)nonanedioate identical (n.m.r., i.r. mixed t.l.c.) with that prepared previously.

B.
5-(6-Carboxyhexyl)-1-(3-(tetrahydropyran-2-yloxy)octyl)hydantoin

To a solution of diethyl 2-(3-(tetrahydropyran-2-yloxy)octylamino)nonanedioate (7.8 g) in ethanol (32 ml) was added a solution of potassium cyanate (3.0 g) in water (6 ml). The resulting suspension was stirred and cooled during the gradual addition of 2 N-hydrochloric acid (16.7 ml). The solution was allowed to stand at room temperature for 22 hours, most of the ethanol was evaporated, water was added, and the insoluble oil was extracted with ether. The ether solution was washed with water, dried over magnesium sulphate, and evaporated. The yellow oil so obtained (8.0 g) was dissolved in light petroleum (b.p. 60°-80° C.) and the solution was refluxed for 4 hours, evaporated to dryness, and the residual oil was heated on the steambath for 2 hours to give 5-(6-ethoxycarbonylhexyl)-1-(3-(tetrahydropyran-2-yloxy)octyl)hydantoin as a yellow oil (7.3 g), which was used without further purification.

A solution of the ester (6.2 g) in 0.5 N-sodium hydroxide solution (80 ml) was allowed to stand at room temperature for 2½ hours after which the solution was washed with ether, the aqueous layer was acidified with 2 N-hydrochloric acid, and the precipitated oil was extracted with ether. The washed and dried ether extract was evaporated to give 5-(6-carboxyhexyl)-1-(3-tetrahydropyran-2-yloxy)octyl)hydantoin as a yellow oil.

C. 5-(6-Carboxyhexyl)-1-(3-hydroxyoctyl)hydantoin

This tetrahydropyranyloxy-compound (3.55 g) was dissolved in tetrahydrofuran (28 ml) and 5 N-hydrochloric acid (7 ml) and the solution was left at room temperature for 3½ hours, and then refluxed for 30 minutes. Most of the solvent was evaporated, water was added, and the insoluble oil was extracted with ether. The ether solution was washed with water, dried over magnesium sulphate and evaporated to give 3.15 g. of viscous yellow oil. The oil was purified by chromatography on a column of silica gel, elution first with chloroform and then with a mixture of chloroform and methanol (19:1) giving 5-(6-carboxyhexyl)-1-(3-hydroxyoctyl)hydantoin as a very viscous almost colourless oil, δ0.89 (3H, triplet, —CH$_3$), 2.34 (2H, triplet, —CH$_2$—CO$_2$H), 2.9–4.2 (4H, complex, —CH$_2$—N, CH—N, CH—OH), ca. 5.6 (2H, broad, exchangeable, —CO$_2$H, —OH), ca. 9.0 (1H, broad, exchangeable, NH).

Using the method of Example 1 the above identified hydantoin was also prepared via the corresponding diethyl 2-((3-hydroxyoctyl)amino)nonanedioate.

D. Separation of Diastereomers

The hydantoin resulting from the above described preparations was a viscous oil which by use of HPLC on a column of silica with a mixture of chloroform, methanol and acetic acid (97:2.5:0.5) as solvent was separated into two diastereomers, both of which formed small colourless needles of m.p. 76°–78° C. and 63°–65° C. respectively.

The same diastereomers were prepared by cyclisation of the corresponding diastereomers of formula (III). That is, the mixture of diastereomers of diethyl 2-[(3-hydroxyoctyl)amino]nonanedioate; prepared as in Example 1 was dissolved in ethanol and an ethereal solution of hydrogen chloride was added. The solution was evaporated to dryness to leave the mixture of diastereomeric hydrochlorides as a viscous oil, which partly solidified on standing. Ether was added and the mass was stirred and cooled to give a crystalline solid, which was collected, washed with ether, and dried. The solid was crystallised from ethyl acetate to give small colourless plates, m.p. 95°–96.5°, of a pure hydrochloride. This salt was suspended in dilute sodium hydroxide solution and shaken with ether, and the separated ether solution was washed, dried and evaporated to give one of the diastereomers (A) of diethyl 2-[(3-hydroxyoctyl)amino]nonanedioate as a colourless oil.

The ether filtrate remaining after collection of the original solid hydrochloride was evaporated to leave an oily hydrochloride, which was converted to base as described above to give the almost pure second diastereomer (B) of diethyl 2-[3-hydroxyoctyl)amino]nonanedioate as a colourless oil.

By the method described in Example 1, the above diastereomer (A) was converted into a single diastereomer of 5-(6-carboxyhexyl)-1-(3-hydroxyoctyl)hydantoin, which crystallised from a mixture of ethyl acetate and light petroleum (b.p. 60°–80°) as small colourless needles; m.p. 63°–65°.

Similarly the above diastereomer (B) was converted into the second diastereomer of 5-(6-carboxyhexyl)-1-(3-hydroxyoctyl)hydantoin, which crystallised from ethyl acetate-light petroleum (b.p. 60°–80°) as small colourless needles, m.p. 76°–78°.

E. Interconversion of the diastereomers

A solution of 5-(6-carboxyhexyl)-1-(3-hydroxyoctyl)hydantoin (diastereomer of m.p. 76°–78°) (100 mg) in N-sodium hydroxide solution (3 ml) was allowed to stand at room temperature for 19 hours. The solution was acidified and extracted with ether, and the ether extract was washed with water, dried and evaporated to leave a viscous oil. By means of high performance liquid chromatography this oil was separated into the two diastereomers of 5-(6-carboxyhexyl)-1-(3-hydroxyoctyl)hydantoin, m.p. 76°–78° C. identical with the starting material (ca. 40 mg) and m.p. 63°–65° C. (ca. 40 mg) identical with the diastereomer (A) described above.

In similar fashion, the diastereomer of m.p. 63°–65° C. was converted into a mixture of approximately equal quantitites of itself with the diastereomer of m.p. 76°–78° C., and the pure diastereomers were isolated by means of high performance liquid chromatography.

EXAMPLES 3 TO 27

By a series of reactions analogous to that described in Example 1, using the appropriate vinyl ketones as starting materials, were prepared:

(3a) diethyl 2-((3-oxopentyl)amino)nonanedioate;
(4a) diethyl 2-((3-oxo-4,4-dimethylpentyl)amino)nonanedioate;
(5a) diethyl-2-((3-oxo-4-methylpentyl)amino)nonanedioate;
(6a) diethyl 2-((3-oxononyl)amino)nonanedioate;
(7a) diethyl 2-((3-oxo-4-methyloctyl)amino)nonanedioate;
(8a) diethyl 2-((3-oxodecyl)amino)nonanedioate;
(9a) diethyl 2-((3-oxo-4,4-dimethyloctyl)amino)nonanedioate;
(10a) diethyl 2-((3-oxo-4-ethylhexyl)amino)nonanedioate;
(11a) diethyl 2-((3-cyclobutyl-3-oxopropyl)amino)nonanedioate;
(12a) diethyl 2-((3-cyclopentyl-3-oxopropyl)amino)nonanedioate;
(13a) diethyl 2-((3-oxo-4,4-dimethyl-5-(3-trifluoromethylphenyl)pentyl)amino)nonanedioate;
(14a) diethyl 2-((3-cyclohexyl-3-oxopropyl)amino)nonanediaote;
(15a) diethyl 2-((3-cycloheptyl)-3-oxopropyl)amino)nonanedioate;
(16a) diethyl 2-((3-oxo-4-phenylpropyl)amino)nonanedioate;
(17a) diethyl 2-((3-oxo-4-phenylbutyl)amino)nonanedioate;
(18a) diethyl 2-((3-oxooctyl)amino)pentanedioate;
(19a) diethyl 2-((3-oxooctyl)amino)undecanedioate;
(20a) ethyl 2-((3-oxooctyl)amino)-3-(3-ethoxycarbonylmethoxyphenyl)propionate;
(21a) ethyl 2-((3-oxo-4,4-dimethylpentyl)amino)-3-(3-ethoxycarbonylmethoxyphenyl)propionate;
(22a) ethyl 2-(3-oxooctylamino)-3-(3-(2-ethoxycarbonylethyl)phenyl)propionate;
(23a) ethyl 2-(3-cyclobutyl-3-oxopropylamino)-3-(3-(2-ethoxycarbonylethylphenyl)propionate;
(24a) ethyl 2-(3-cyclopentyl-3-oxopropylamino)-3-(3-(2-ethoxycarbonylethylphenyl)propionate;
(25a) ethyl 2-(3-cyclohexyl-3-oxopropylamino)-3-(3-(2-ethoxycarbonylethylphenyl)propionate;

(26a) diethyl 2-(3-oxooctylamino)-7-oxanonanedioate; and (27a) diethyl 2-(3-cyclopentyl-3-oxopropylamino)-7-oxanonanedioate; which were converted to the corresponding hydroxy compounds:

(3b) diethyl 2-((3-hydroxypentyl)amino)nonanedioate;

(4b) diethyl 2-((3-hydroxy-4,4-dimethylpentyl)amino)nonanedioate;

(5b) diethyl 2-((3-hydroxy-4-methylpentyl)amino)nonanedioate;

(6b) diethyl 2-((3-hydroxynonyl)amino)nonanedioate;

(7b) diethyl 2-((3-hydroxy-4-methyloctyl)amino)nonanedioate;

(8b) diethyl 2-((3-hydroxydecyl)amino)nonanedioate;

(9b) diethyl 2-((3-hydroxy-4,4-dimethyloctyl)amino)nonanedioate;

(10b) diethyl 2-((3-hydroxy-4-ethylhexyl)amino)nonanedioate;

(11b) diethyl 2-((3-cyclobutyl-3-hydroxypropyl)amino)nonanedioate;

(12b) diethyl 2-((3-cyclopentyl-3-hydroxypropyl)amino)nonanedioate;

(13b) diethyl 2-((3-hydroxy-4,4-dimethyl-5-(3-trifluoromethylphenyl)pentyl)amino)nonanedioate;

(14b) diethyl 2-((3-cyclohexyl-3-hydroxypropyl)amino)nonanedioate;

(15b) diethyl 2-((3-cycloheptyl-3-hydroxypropyl)amino)nonanedioate;

(16b) diethyl 2-((3-hydroxy-3-phenylpropyl)amino)nonanedioate;

(17b) diethyl 2-((3-hydroxy-4-phenylbutyl)amino)nonanedioate;

(18b) diethyl 2-((3-hydroxyoctyl)amino)pentanedioate;

(19b) diethyl 2-((3-hydroxyoctyl)amino)undecanedioate;

(20b) ethyl 2-((3-hydroxyoctyl)amino)-3-(3-ethoxycarbonylmethoxyphenyl)propionate;

(21b) ethyl 2-((3-hydroxy-4,4-dimethylpentyl)amino)-3-(3-ethoxycarbonylmethoxyphenyl)propionate;

(22b) ethyl 2-((3-hydroxyoctylamino)-3-(3-(2-ethoxycarboylethyl)phenyl)propionate;

(23b) ethyl 2-((3-cyclobutyl-3-hydroxypropylamino)-3-(3-(2-ethoxycarbonylethylphenyl)-propionate;

(24b) ethyl 2-((3-cyclopentyl-3-hydroxypropylamino-3-(3-(2-ethoxycarbonylethylphenyl)propionate;

(25b) ethyl 2-(3-cyclohexyl-3-hydroxypropylamino)-3-(3-(2-ethoxycarbonylethylphenyl)propionate;

(26b) diethyl 2-(3-hydroxyoctylamino)-7-oxanonanedioate; and (27b) diethyl 2-(3-cyclopentyl-3-hydroxypropylamino)-7-oxa-nonanedioate from which are prepared the following hydantoins of formula (I) which where indicated were separated by HPLC to provide two diastereomers having the stated melting points.

(3c) 5-(6-carboxyhexyl)-1-(3-hydroxypentyl)hydantoin, a colourless oil, diastereomers 71°–73° and 56°–58°;

(4c) 5-(6-carboxyhexyl)-1-(3-hydroxy-4,4-dimethylpentyl)hydantoin, diastereomers 114°–115° and 144°–146°;

(5c) 5-(6-carboxyhexyl)-1-(3-hydroxy-4-methylpentyl)hydantoin, m.p. ca. 70°–80°, diastereomers 73°–76° and 110 –111°;

(6c) 5-(6-carboxyhexyl)-1-(3-hydroxynonyl)hydantoin, a viscous oil;

(7c) 5-(6-carboxyhexyl)-1-(3-hydroxy-4-methyloctyl)hydantoin, a viscous oil;

(8c) 5-(6-carboxyhexyl)-1-(3-hydroxydecyl)hydantoin, a viscous oil, diastereomers 68°–70° and 82°–83°;

(9c) 5-(6-carboxyhexyl)-1-(3-hydroxy-4,4-dimethyloctyl)hydantoin as colourless crystals, m.p. 90°–98°, one diastereomer isolated by crystallisation from ethyl acetate m.p. 103°–104°;

(10c) 5-(6-carboxyhexyl)-1-(3-hydroxy-4-ethylhexyl)hydantoin, m.p. 70°–80°, diastereomers 82°–84° and 120°–122°;

(11c) 5-(6-carboxyhexyl)-1-(3-cyclobutyl-3-hydroxypropyl)hydantoin, diastereomers 114°–116° and 103°–105°;

(12c) 5-(6-carboxyhexyl)-1-(3-cyclopentyl-3-hydroxypropyl)hydantoin, diastereomers 116°–117° and 97°–99°;

(13c) 5-(6-carboxyhexyl)-1-(3-hydroxy-4,4-dimethyl-5-m-trifluoromethylphenylpentyl)hydantoin, diastereomers 118°–120° and 145°–147°;

(14c) 5-(6-carboxyhexyl)-1-(3-cyclohexyl-3-hydroxypropyl)hydantoin, diastereomers 96°–98° and 124°–126°;

(15c) 5-(6-carboxyhexyl)-1-(3-cycloheptyl-3-hydroxypropyl)hydantoin, m.p. ca. 70°–76°, diastereomers 107°–109° and 107°–109°;

(16c) 5-(6-carboxyhexyl)-1-(3-hydroxy-3-phenylpropyl)hydantoin, diastereomers both forming colourless viscous oils;

(17c) 5-(6-carboxyhexyl)-1-(3-hydroxy-4-phenylbutyl)hydantoin, diastereomers 102°–104° and 61°–63°;

(18c) 5-(3-carboxypropyl)-1-(3-hydroxyoctyl)hydantoin, diastereomers both forming colourless viscous oils;

(19c) 5-(8-carboxyoctyl)-1-(3-hydroxyoctyl)hydantoin, diastereomers 57°–60° and 69°–71°;

(20c) 5-(3-carboxymethoxybenzyl)-1-(3-hydroxyoctyl)hydantoin, a colourless meringue;

(21c) 5-(3-carboxymethoxybenzyl)-1-(3-hydroxy-4,4-dimethylpentyl)hydantoin; diastereomers of the corresponding ethyl ester m.p. 100°–103° and 151°–154°;

(22c) 5-(3-(2-carboxyethylbenzyl))-1-(3-hydroxyoctyl)hydantoin; one diastereomer m.p. 82°–86°;

(23c) 5-(3-(2-carboxyethylbenzyl))-1-(3-cyclobutyl-3-hydroxypropyl)hydantoin; one diastereomer 118°–121°;

(24c) 5-(3-(2-carboxyethylbenzyl))-1-(3-cyclopentyl-3-hydroxypropyl)hydantoin; one diastereomer 140°–143°;

(25c) 5-(3-(2-carboxyethylbenzyl))-1-(3-cyclohexyl-3-hydroxypropyl)hydantoin;

(26c) 5-(4-carboxymethoxybutyl)-1-(3-hydroxyoctyl)hydantoin; and (27c) 5-(4-carboxymethoxybutyl)-1-(3-cyclopentyl-1-hydroxypropyl)hydantoin; all of which were obtained via the corresponding ethyl ester.

Starting materials used in the above procedures were prepared as follows:

A. EXAMPLES 18 AND 19

Using the procedure described in Example 1A were prepared diethyl 2-aminopentanedioate, b.p. 93°–96°/0.02 mm $n_D^{24}$ 1.4425 and diethyl 2-aminoandecanedioate b.p. 160°/0.1 mm which were used in Examples 18 and 19 respectively.

B. Ethyl 2-amino-3-(3-ethoxycarbonylmethoxyphenyl)propionate

Diethyl acetamidomalonate (2.60 g) and ethyl 3-(chloromethyl)phenoxyacetate (Robertson, J. Chem. Soc. (1933), 492; U.S. Pat. No. 3,933,895) (2.39 g) were dissolved in ethanolic ethoxide (prepared from sodium (230 mg) and absolute ethanol (10 ml)) and the mixture refluxed for 19 hours. The cooled solution was poured into ice-water, the product was extracted into ether, and the dried extract evaporated. The residual gum was crystallised from ether/hexane to give diethyl acetamido-(3-ethoxycarbonylmethoxyphenyl)malonate as white prisms, m.p. 98.5°–101.5°. This derivative (1.90 g) was refluxed with 10% aqueous hydrochloric acid (25 ml) for 3½ hours and the cooled solution was evaporated to dryness in vacuo. The residual white solid was dissolved in the minimum quantity of absolute ethanol and added dropwise to a stirred, cooled (−10° C.) mixture of absolute ethanol (15 ml) and thionyl chloride (1.64 g). The resulting solution was set aside at room temperature for 18 hours, refluxed for 1 hour, cooled, and poured into ice-water, adjusting the pH to 9–10 with aqueous sodium hydroxide. The mixture was extracted with ether, and the dried extract was concentrated, giving ethyl 2-amino-3-(3-ethoxycarbonylmethoxyphenyl)propionate as a colourless oil, which was used without further purification in Examples 20 and 21.

C. Ethyl 2-amino-3-(3-(2-ethoxycarbonylethyl)phenyl)propionate

A solution of di-isopropylamine (4.04 g) and butyllithium (25 ml, 1.60 M in hexane) in dry tetrahydrofuran (40.0 ml), stirred at −78° under dry nitrogen, was treated over 5 minutes with t-butyl acetate (4.64 g). To this solution was added, over 5 minutes, a solution of α,α'-dibromo-m-xylene (11.60 g) and dry hexamethylphosphoramide (1.42 g) in dry tetrahydrofuran (8.0 ml). The resulting yellow solution was stirred at −78° for ½ hour, then allowed to warm to room temperature over 3 hours. Excess ice-water was added, and the mixture extracted with ether, and the extract washed with 1 N hydrochloric acid (60 ml) then water. The dried extract was concentrated in vacuo, to give a yellow oil which was purified by column chromatography on silica, eluting with 1:1 ether:hexane, giving t-butyl 3-(3-bromomethylphenyl)propionate as a colourless oil. Using the method described in the last foregoing paragraph this was converted to the desired diethylester which was used in each of Examples 22 to 25.

D. Diethyl 2-amino-7-oxa-nonanedioate

This was prepared from ethyl 4-bromobutoxyacetate (Merck, Ger. Offen. 2,354,085) by a series of reactions analogous to that described in paragraph B above and was obtained as a colourless oil, b.p. 120°–121°/0.005 mm. It was used in Examples 26 and 27.

EXAMPLE 28

Preparation of 5-(6-carboxyhexyl)-1-(3-oxooctyl)hydantoin

Diethyl 2-(3-oxooctylamino)nonanedioate (7.7 g) prepared by the method described in Example 1B was treated with potassium cyanate and hydrochloric acid to give 5-(6-ethoxycarbonylhexyl)-1-(3-oxo-octyl)hydantoin. Hydrolysis of this ester using sodium hydroxide solution gave 5-(6-carboxyhexyl)-1-(3-oxooctyl)hydantoin as a viscous oil, which crystallised to a low-melting solid.

EXAMPLE 29

Preparation of 5-(6-carboxyhexyl)-1-(5-phenylpentyl)hydantoin

A mixture of diethyl 2-aminononanedioate (25.9 g) and 5-phenylpentyl bromide (22.7 g) was heated in a bath at 100° C. for 3 hours. After cooling, ether (100 ml) was added to the mixture, which was then allowed to stand for 2 hours, at 0° C. The colourless solid (21.95 g) which crystallised was collected and dried. This diethyl (2-((5-phenylpentyl)amino)nonanedioate hydrobromide melted at 70°–72° C.

A solution of this hydrobromide (4.86 g) in ethanol (20 ml) and 2 N-hydrochloric acid (5 ml) was cooled in ice and stirred during the gradual addition of a solution of potassium cyanate (1.62 g) in water (5 ml), after which the solution was allowed to stand at room temperature for 18 hours. The alcohol was evaporated, water was added, the insoluble oil was extracted with ether, and the ethereal extract was dried and evaporated to leave a pale yellow oil. This material was heated on the steam bath for 6 hours to give 5-(6-ethoxycarbonylhexyl)-1-(5-phenylpentyl)hydantoin.

The foregoing ester (4.0 g) was hydrolysed by treatment with dilute sodium hydroxide solution and the product was purified by chromatography on silica gel, to give 5-(6-carboxyhexyl)-1-(5-phenylpentyl)hydantoin crystallising from ethyl acetate-light petroleum (b.p. 60°–80° C.) in colourless prismatic needles, m.p. 90°–92° C.

EXAMPLES 29 TO 35

By a series of reactions analogous to that described in Example 28 using the appropriate alkyl halides were prepared:

(29a) diethyl 2-octylaminononanedioate;
(30a) diethyl 2-(4-propoxybutyl)aminononanedioate;
(31a) diethyl 2-(4-phenoxybutyl)aminononanedioate;
(32a) diethyl 2-(4-m-trifluoromethylphenoxybutyl)aminononanedioate;
(33a) diethyl 2-(3-m-tolyloxypropyl)aminononanedioate;
(34a) diethyl 2-(3-hydroxypropyl)aminononanedioate; and
(35a) diethyl 2-(3-hydroxy-3-methyloctyl)aminononanedioate which were converted to the desired hydantoins:
(29b) 5-(6-ethoxycarbonylhexyl)-1-octylhydantoin, m.p. 46°–48°;
(29c) 5-(6-carboxyhexyl)-1-octylhydantoin, m.p. 88°–89°;
(30b) 5-(6-carboxyhexyl)-1-(4-propoxybutyl)hydantoin, m.p. 72°–74°;
(31b) 5-(6-carboxyhexyl)-1-(4-phenoxybutyl)hydantoin, m.p. 88°–90°;
(32b) 5-(6-carboxyhexyl)-1-(4-m-trifluoromethylphenoxybutyl)hydantoin, m.p. 51°–54°;
(33b) 5-(6-carboxyhexyl)-1-(3-m-tolyloxypropyl)hydantoin, a colourless viscous oil;
(34b) 5-(6-carboxyhexyl)-1-(3-hydroxypropyl)hydantoin, m.p. 111°–113°; and
(35b) 5-(6-carboxyhexyl)-1-(3-hydroxy-3-methyloctyl)hydantoin, a viscous oil.

EXAMPLE 36

Preparation of 1-(6-Carboxyhexyl)-5-octyl hydantoin

2-Aminodecanoic acid (J. Am. Chem. Soc., 1946, 68, 450) (16.0 g) was added in portions to a cooled (−10° C.) mixture of absolute ethanol (70 ml) and thionyl chloride (6 ml) with stirring. The resulting solution was set aside for 2 hours, at room temperature, refluxed for 1 hour, cooled, poured into ice-water, and the pH of the solution was adjusted to 9 with aqueous sodium hydroxide. The mixture was extracted with ether, the extract was dried, concentrated, then distilled, giving ethyl 2-aminodecanoate (75%) as a colourless oil, b.p. 82°–84° C./0.2 mm.

A solution of the above aminoester (18 g) and ethyl 7-bromoheptanoate (20 g) in absolute ethanol (50 ml) was refluxed for 24 hours, and the ethanol was then evaporated. Addition of ether precipitated a hydrobromide salt, m.p. 98° C., which was dissolved in a little dichloromethane, treated with an equivalent of triethylamine, washed thoroughly with water, and dried; removal of the solvent gave ethyl 2-(6-ethoxycarbonylhexylamino)decanoate (52%) as a colourless viscous oil, b.p. 142°–144° C./0.001 mm.

Ethyl 2-(6-ethoxycarbonylhexylamino)decanoate (7.4 g) was reacted with potassium cyanate and hydrochloric acid to give 1-(6-ethoxycarbonylhexyl)-5-octylhydantoin which formed colourless crystals, m.p. 68°–70° C., from light petroleum (b.p. 60°–80° C.).

This ester (4.0 g) was hydrolysed with sodium hydroxide solution to give 1-(6-carboxyhexyl)-5-octylhydantoin which crystallised from a mixture of ethyl acetate and light petroleum (b.p. 60°–80° C.) as colourless needles, m.p. 65°–66° C.

EXAMPLE 37

Preparation of 5-(6-carboxyhexyl)-3-methyl-1-octylhydantoin

A solution of diethyl 2-octylaminononanedioate (742 mg) and methyl isocyanate (120 mg) in dry ether (7.5 ml) was allowed to stand at room temperature for 48 hours, after which time the ether was evaporated to leave a pale yellow oil (800 mg). The oil was heated on the steam bath for 2 hours to give 5-(6-ethoxycarbonyl)-3-methyl-1-octylhydantoin as a yellow oil.

The ester (650 mg) was hydrolysed by standing in solution in ethanol (2.4 ml) and 5 N-sodium hydroxide solution (0.6 ml) for 3 hours at room temperature. After evaporation of the ethanol, the acidic product was isolated by extraction with ether, and purified by chromatography on a column of silica gel to give 5-(6-carboxyhexyl)-3-methyl-1-octylhydantoin as a colourless oil.

EXAMPLE 38

Preparation of 5-(6-carboxyhexyl)-3-methyl-1-(3-hydroxyoctyl)hydantoin

Diethyl 2-((3-oxooctyl)amino)nonanedioate (Example 28) was allowed to react with methyl isocyanate as described in Example 37 to give 5-(6-ethoxycarbonylhexyl)-3-methyl-1-(3-oxooctyl)hydantoin, which was hydrolysed to 5-(6-carboxyhexyl)-3-methyl-1-(3-oxooctyl) hydantoin a colourless oil.

This keto-acid (1.23 g) was dissolved in 0.25 N-sodium hydroxide solution (15 ml) and the solution was stirred in an ice-bath during the addition of sodium borohydride (63 mg). After 3 hours' stirring at room temperature, the solution was acidified and extracted with ether. The washed and dried ether extract was evaporated to leave an oil which was purified by chromatography on a column of silica using a mixture of chloroform and methanol (50:1) as eluant to give 5-(6-carboxyhexyl)-3-methyl-1-(3-hydroxyoctyl)hydantoin as a colourless viscous oil.

EXAMPLE 39

Preparation of 1-(6-Carboxyhexyl)-3-methyl-5-octylhydantoin

By the method described in Example 37, ethyl 2-(6-ethoxycarbonylhexylamino)decanoate (Example 36) was converted into 1-(6-ethoxycarbonylhexyl)-3-methyl-5-octylhydantoin, and thence by hydrolysis into 1-(6-carboxyhexyl)-3-methyl-5-octylhydantoin, isolated as a colourless oil.

EXAMPLE 40

Preparation of 3-Butyl-5-(6-carboxyhexyl)-1-octylhydantoin

To a solution of sodium (308 mg) in ethanol (40 ml) was added 5-(6-ethoxycarbonylhexyl)-1-octylhydantoin (see Example 29b), followed by butyl bromide (1.8 g), and the solution was refluxed for 24 hours. The solvent was evaporated, water was added and the insoluble oil was extracted with ether. The washed and dried extract was evaporated to give 3-butyl-5-(6-ethoxycarbonylhexyl)-1-octylhydantoin.

This ester (3.2 g) was dissolved in ethanol (15 ml) and 2 N-sodium hydroxide (15 ml) and left at room temperature for 1 hour. The acidic product was isolated by extraction with ether and purified by chromatography on silica gel to give 3-butyl-5-(6-carboxyhexyl)-1-octyl hydantoin as a colourless oil.

EXAMPLE 41

Preparation of 3-Butyl-1-(6-carboxyhexyl)-5-octylhydantoin

By the method of Example 40, 1-(6-ethoxycarbonylhexyl)-5-octylhydantoin (see Example 36) was converted into 3-butyl-1-(6-ethoxycarbonylhexyl)-5-octylhydantoin, which was hydrolysed to give 3-butyl-1-(6-carboxyhexyl)-5-octylhydantoin as a colourless oil.

EXAMPLE 42

Preparation of 5-(6-Carboxyhex-2-ynyl)-1-(3-hydroxyoctyl)hydantoin

Under the reaction conditions described in Example 1A diethyl acetamidomalonate and methyl 7-bromohept-5-ynoate reacted to give diethyl acetamido-(6-methoxycarbonylhex-2-ynyl)malonate as a yellow oil.

This crude product was hydrolysed by boiling with 5N-hydrochloric acid, and the product was re-esterified to give diethyl 2-aminonon-4-ynedioate, which was distilled to give a colourless oil, b.p. 116°/0.01 mm, $n_D^{17}$ 1.4703.

The foregoing amino-compound was reacted with oct-1-en-3-one to give diethyl 2-((3-oxooctyl)amino)-non-4-ynedioate which was reduced with sodium borohydride to give diethyl 2-((3-hydroxyoctyl)amino)-4-ynedioate.

Treatment of this compound with potassium cyanate and hydrochloric acid, and hydrolysis of the hydantoin ester so produced gave a light brown oil. Purification by chromatography o a column of silica with a mixture of chloroform and methanol (30:1) as eluante gave 5-(6-carboxyhex-2-ynyl)-1-(3-hydroxyoctyl)hydantoin as a colourless oil, (mixture of diastereomers) showing two spots, Rf. 0.38, 0.44, when run in a chloroform, methanol, acetic acid (90:5:5) mixture on a thin layer of silica. By use of HPLC one of the diastercomeis (TLC, Rf. 0.38) was isolated as a colourless oil; NMR (CDCl$_3$)$\delta$0.89 (3H, triplet, —CH$_3$), 2.2–2.4 (6H, multiplet, —CH$_2$, C=C.CH$_2$—+—CH$_2$.CO$_2$H), 3.54 (2H, triplet, >N.CH$_2$—), ca 3,6 (1H, multiplet, >CH.OH), 4.11 (1H, triplet, >N.CH.CO—).

This compound was then catalytically hydrogenated to the corresponding 5-(6-carboxyhex-2-enyl)-1-(3-hydroxyoctyl) hydantoin and subsequently to the corresponding saturated compound which was found to be identical with the title compound of Example 2.

EXAMPLE 43

A. 2-(Dibutoxymethyl)glycine ethylester

N-Formylglycine ethyl ester was C-formylated using a method based on that described by Harman and Hutchinson in J. Org. Chem. 1975 40, 3474 and the resulting compound converted to 2-(dibutoxymethyl)glycine ethyl ester using the method described in "Chemistry of Penicillin", Eds. H. T. Clarke et al., published by Princetown University Press, New Jersey, 1949 p. 517.

B. 1-(6-Carboxyhexyl)hydantoin-5-carboxaldehyde

A mixture of 2-(dibutoxymethyl)glycine ethyl ester (2.0 g.) with ethyl 7-bromoheptanoate (1.82 g.) was heated under nitrogen in a bath at 100° C. for 3 hr. to give crude ethyl 7-((2,2-dibutoxy-1-ethoxycarbonylethyl)amino)-heptanoate hydrobromide. A stirred solution of 3.28 g. of this hydrobromide in ethanol (13 ml) was cooled in ice-water and treated with a solution of potassium cyanate (1.34 g) in water (4 ml), followed by 2N aqueous hydrochloric acid (3.63 ml); the cooling bath was removed and stirring was continued at room temperature for 22 hr. The ethanol was evaporated in vacuo, the residue was shaken with water and ether, and the ethereal solution was separated, washed with water and dried over magnesium sulphate (MgSO$_4$); removal of the ether left an oil which was heated under nitrogen at 100° C. for 3 hr., to give 5-dibutoxymethyl-1-(6-ethoxycarbonylhexyl)hydantoin (2.94 g.). This was stirred in ether (6 ml) with water (48 ml) and N aqueous sodium hydroxide (24.9 ml) at room temperature for 1½ hr. and, after the addition of more ether (50 ml), the aqueous phase was separated, cooled (ice-H$_2$O), stirred with fresh ether and acidified to Congo Red with N aqueous hydrochloric acid. The ethereal solution of carboxylic acid was thrice washed with water, dried (MgSO$_4$), and evaporated, to leave 1-(6-carboxyhexyl)-5-dibutoxymethylhydantoin (2.15 g.) as a gum. When 1.89 g. of the latter were cooled in ice-water and stirred with concentrated aqueous hydrochloric acid (8.5 ml), the resulting solution gave place spontaneously to a suspension of colourless crystals. The suspension was set aside at room temperature for 1½ hr., diluted with water (10 ml.) and set aside 15 min.; the crystals were then collected, washed with water, dried in vacuo, suspended in ether (3 ml), and collected again, to give 1-(6-carboxyhexyl)hydantoin-5-carboxaldehyde (0.74 g.), m.p. 223.5°–225° C. (Found: C. 51.86- H, 6.66; N, 10.62. C$_{11}$H$_{16}$N$_2$O$_5$ required C, 51.56; H, 6.29; N, 10.93%). In dimethyl sulphoxide-d$_6$, this compound exists predominantly as the masked aldehyde, 1-((6-carboxyhexyl)-5-hydroxymethylenehydantoin.

C.

1-(6-Carboxyhexyl)-5-((E)-3-oxo-octylidene)hydantoin

A mixture of 1-(6-carboxyhexyl)hydantoin-5-carboxaldehyde (20 mg.) with 2-oxoheptylidene-triphenylphosphorane (59 mg.) (see J. Org. Chem. (1972) 37, 1818) and 1 drop of benzene was heated under nitrogen at 100° C. for 35 min., and the resulting gum was taken up in ethyl acetate. The product was extracted into dilute aqueous sodium bicarbonate, the extract was washed with ethyl acetate and acidified to Congo Red with N aqueous hydrochloric acid, and the liberated carboxylic acid was extracted into ether. The ethereal solution was washed with water, dried (MgSO$_4$), and evaporated, to give a gum (25 mg.) which was identified by 'H n.m.r. spectroscopy (characteristic signals at $\delta$5.72 (1H, triplet, =GH—) and 3.93 (2H, doublet, =CH—CH$_2$—CO) with J 7.1 Hz, in deuterochloroform) as 1-(6-carboxyhexyl)-5-((E)-3-oxo-octylidene)hydantoin.

D.

1-(6-Carboxyhexyl)-5-((E)-3-hydroxyoctylidene)-hydantoin

A stirred solution of 1-(6-carboxyhexyl)-5-((E)-3-oxooctylidene)hydantoin (20 mg.) in H$_2$O (1.5 ml.) containing a slight excess of sodium bicarbonate was treated with sodium borohydride (5 mg.). After 60 min., the solution was acidified to Congo Red with N aqueous hydrochloric acid, the liberated carboxylic acid was extracted into ethyl acetate, and the ethyl acetate solution was thrice washed with water and dried (MgSO$_4$). Evaporation of the ethyl acetate left a pale yellow gum (14 mg.) which was identified by 'H n.m.r. spectroscopy (characteristic signal at $\delta$5.61 (1H, triplet =CH—, J 7.1 Hz) in deuterochloroform as 1-(6-carboxyhexyl)-5-((E)-3-hydroxyoctylidene)hydantoin.

E. 1-(6-Carboxyhexyl)-5-(3-hydroxyoctyl)hydantoin

The product described in paragraph C was substantially reduced to 1-(6-carboxyhexyl)-5-(3-oxooctyl)-hydantoin and the title compound which were found to be identical with the title compounds of Examples 28 and 2 respectively.

In the following examples the hydantoins are designated thus:

Compound 2: 5-(6-Carboxyhexyl)-1-(3-hydroxyoctyl)-hydantoin

Compound 4: 5-(6-Carboxyhexyl)-1-(3-hydroxy-4,4-dimethylpentyl)hydantoin

Compound 6: 5-(6-Carboxyhexyl)-1-(3-hydroxynonyl)-hydantoin

Compound 9: 5-(6-Carboxyhexyl)-1-(3-hydroxy-4,4-dimethyloctyl)hydantoin

Compound 11: 5-(6-Carboxyhexyl)-1-(3-hydroxy-3-cyclobutylpropyl)hydantoin

Compound 12: 5-(6-Carboxyhexyl)-1-(3-hydroxy-3-cyclopentylpropyl)hydantoin

Compound 14: 5-(6-Carboxyhexyl)-1-(3-hydroxy-3-cyclohexylpropyl)hydantoin

Compound 38: 5-(6-Carboxyhexyl)-3-methyl-1-(3-oxooctyl)hydantoin.

Where a particular diastereomer is used, this is indicated by reference to its melting point.

EXAMPLE A

Cardiovascular effects in rats

Male normotensive rats Wistar (Charles River) strain, (250–350 g) were anesthetised (chloroform) prior to cannulation of the left femoral vein and anaesthesia maintained by intravenous chloralose (60 mg/kg). Pulsatile blood pressure was recorded from the left femoral artery with an electronic transducer (Bell and Howell Type 4-327 L221) and integrated heart rate was measured with a cardiotachometer triggered from the arterial pressure waves. The test compound was administered as a solution in physiological saline by intravenous injection via the femoral cannula. The responses recorded were allowed to return to the preinjection levels between successive administrations.

Injections of the vehical alone in volumes equivalent to those containing drug did not produce hypotension.

| Compound | Dose | Mean fall in blood pressure mmHg |
| --- | --- | --- |
| $PGE_2$ | 4µg/kg | 28 |
| $PGE_2$ | 16µg/kg | 44 |
| Compound 2 | 10µg/kg | 14 |
| Compound 2 | 1mg/kg | 42 |
| Compound 6 | 3mg/kg | 40 |
| Compound 9 | 3mg/kg | 22 |

EXAMPLE B

Inhibition of Platelet Aggregation

Aggregation of platelets in 1 ml. of fresh human platelet rich plasma (PRP) was monitored in a Born aggregometer.

The compound to be tested was added to the PRP at the desired concentration, and the resulting mixture incubated at 37° C. for 1 minute after which platelet aggregation was stimulated by the addition of adenosine diphosphate (ADP) to a concentration of 5 µM.

The anti-aggregatory effect of the compound was assessed by measuring the percentage inhibition of platelet aggregation in the presence of the compound as compared when it was completely absent.

| Compound | Concentration | % Inhibition of Aggregation |
| --- | --- | --- |
| $PGE_1$ | 15ng/ml | 33 |
| $PGE_1$ | 20ng/ml | 47 |
| $PGE_1$ | 30ng/ml | 63 |
| $PGE_1$ | 40ng/ml | 69 |
| Compound 12 (m.p. 116°–117°) | 0.5ng/ml | 25 |
| Compound 12 (m.p. 116°–117°) | 1.0ng/ml | 51 |
| Compound 12 (m.p. 116°–117°) | 2.0ng/ml | 79 |
| Compound 12 (m.p. 116°–117°) | 4.0ng/ml | 94 |

Using comparisons such as this the following relative potencies were demonstrated with respect to $PGE_1$. Compound 2 (m.p. 76°–78°), 12.5x; Compound 4 (m.p. 144°–146°), 0.05x; Compound 11 (114°–116°), 5.2x; Compound 12 (m.p. 116°–117°), 12.5x; and Compound 14 (m.p. 96°–98°), 16x.

EXAMPLE C

Compound 38 was found to reduce aspirin-indused gastric ulceration in rats: an oral dose of 1 mg/kg gave 80% protection.

EXAMPLE D

At an intravenous dose of 30 µg/kg, Compound 2 completely inhibited pentagastrin-induced gastric acid secretion in rats.

EXAMPLE E

An intravenous injection of Compound 9 (50 µg/kg) was found to completely anatagonise histamine-reduced broncho-constriction in anaesthetised guinea-pigs.

EXAMPLE F

Intravenous infusions of Compound 2 (m.p. 76°–78° C.) at a dose of 250 µg/min have been found to reduce electrically-induced arterial thrombosis in anaesthetised rabbits.

EXAMPLE G

| Tablet | In one tablet |
| --- | --- |
| Compound 12 (m.p. 116°–117°) | 5.0 mg |
| Lactose B.P. | 82.0 mg |
| Starch B.P. | 10.0 mg |
| Povidone B.P.C. | 2.0 mg |
| Magnesium Stearate | 1.0 mg |

Mix together the Compound 12, lactose and starch. Granulate the powders using a solution of the povidone in Purified Water. Dry the granules, add the Magnesium Stearate and compress to produce tablets, 100 mg per tablet.

EXAMPLE H

| Capsule | In one capsule |
| --- | --- |
| Compound 12 (m.p. 116°–117°) | 10 mg |
| Lactose | 79 mg |
| Starch | 10 mg |
| Magnesium Stearate | 1 mg |

Mix the powders in a powder blender, fill into hard gelatin capsules, 100 mg per capsule.

EXAMPLE I

| 1 µg/ml Injection | |
| --- | --- |
| Compound 12 (m.p. 116°–117°) | 100 µg |
| Water for Injection to | 100 ml |

Dissolve the Compound 12 in the Water for Injection. Sterilise the solution by filtration through a membrane filter, 0.22 µm pore size, collecting the filtrate in a sterile receiver. Under aseptic conditions, fill the solution into sterile glass ampoules, 1 ml per ampoule. Seal by fusion of the glass.

EXAMPLE J

| 10 µg/ml Injection | |
| --- | --- |
| Compound 12 (m.p. 116°–117°) | 1 mg |
| Ethyl Alcohol | 10 ml |
| Propylene Glycol | 30 ml |

| -continued | |
|---|---|
| 10 μg/ml Injection | |
| Water for Injection to | 100 ml |

Dissolve the Compound 12 in the Ethyl Alcohol, add the Propylene glycol and dilute to volume with Water for Injection.

Sterilise the solution by filtration through a membrane filter, 0.22 μm pore size, collecting the filtrate in a sterile vessel. Under aseptic conditions, fill the solution into sterile glass vials, 10 ml per vial. Close with a sterile rubber plug and secure with an aluminium collar.

EXAMPLE K

| 100 μg Single dose injection (freeze-dried) | |
|---|---|
| Compound 12 (m.p. 116°–117°) | 10.0 mg |
| Mannitol | 2.5 g |
| N/10 Sodium Hydroxide Solution | qs to pH 10.0 |
| Water for Injection to | 100.0 ml |

Suspend the Compound 12 in approximately 20 ml Water. Add sufficient Sodium Hydroxide Solution to produce pH 10 and stir to dissolve the Compound 12. Add and dissolve the Mannitol and dilute to volume with Water for Injection.

Sterilise the solution by passage through a membrane filter, 0.22 μm pore size and distribute aseptically into sterile vials, 1 ml per vial. Freeze dry the solutions and seal the containers under aseptic conditions with rubber closures. Each vail contains 100 μg Compound 12 as its freeze-dried Sodium salt.

EXAMPLE L

| Suppository | |
|---|---|
| Compound 12 (m.p. 116°–117°) | 3 mg |
| Massa Esterinum C to | 2 mg |

Melt the suppository base at around 40° C. Gradually incorporate the Compound 12 in fine powder and mix until homogeneous Pour into suitable moulds and allow to set.

Massa Esterinum C is a commerically available suppository base consisting of a mixture of mono-, di- and tri-glycerides of saturated vegetable fatty acids. It is marketed by Henkel International, Dusseldorf.

What we claim is:

1. A compound of formula

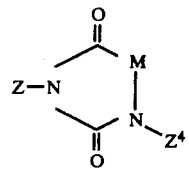

wherein
Z is hydrogen or alkyl;
M is >C=$Z^3$, >CH—CHO or >CH—CH(O$G^3$)$_2$, $G^3$ being alkyl; and
$Z^4$ is —CH$_2$—X—$X^1$—$X^2$ or —Y—$Y^1$—$Y^2$—$Y^3$, except when M is C=$Z^3$ whereupon
either
$Z^3$ is =CR—CH$_2$—$Y^1$—$Y^2$—$Y^3$ and $Z^4$ is —CH$_2$—X—$X^1$—$X^2$, or
$Z^3$ is =CH—X—$X^1$—$X^2$ and $Z^4$ is —Y—$Y^1$—$Y^2$—$Y^3$;
wherein
R is hydrogen or methyl;
X is phenylene, —C≡C—, —CH=CH— or —CH$_2$—CQ$_2$—, in which each Q is independently selected from hydrogen and alkyl or the two Q's together form an alkylene radical having four, five or six carbon atoms;
$X^1$ is a covalent bond or a straight or branched alkylene chain having 1 to 6 carbon atoms, optionally having one of its methylene groups replaced by oxa (—O—) provided that at least one carbon atom separates the oxa group from a —C≡C—, —CH=CH— or —CO— group;
$X^2$ is selected from 5-tetrazolyl, carboxyl, carboxamide, hydroxymethylene and alkoxycarbonyl;
Y is —CR$_2$—CH$_2$— in which each R is independently as defined above;
$Y^1$ is carbonyl, methylene, methylene substituted by hydroxyl, or methylene substituted by hydroxyl and alkyl;
$Y^2$ is a covalent bond or straight or branched alkylene having 1 to 7 carbon atoms, optionally substituted on the carbon adjacent $Y^1$ by one or two groups independently selected from alkyl, cycloalkyl and bicycloalkyl; and
$Y^3$ is hydrogen, hydroxy, alkoxy having 1 to 7 carbon atoms, cycloalkyl, bicycloalkyl, phenyl, benzyl, phenoxy or benzyloxy,
wherein each of phenyl, benzyl, phenoxy and benzyloxy may be substituted in the benzene ring by one or more groups selected from hydroxy, halogeno, nitro, amino, acylamino, alkenyl, alkoxy, phenyl, and alkyl which may itself be substituted by one or more halogeno groups; or
Y is a bond, —CH$_2$— or —CH$_2$.CH$_2$—; and
$Y^1$, $Y^2$ and $Y^3$ taken together form a cycloalkyl group substituted by a hydroxyl group;
and salts thereof.

2. The compound is 1-(6-carboxyhexyl)-5-((E)-3-hydroxyoctylidene)hydantoin.

* * * * *